(12) United States Patent
Akiyama et al.

(10) Patent No.: US 11,141,501 B2
(45) Date of Patent: Oct. 12, 2021

(54) GASIFIER FOR STERILIZER

(71) Applicant: Dai Nippon Printing Co., Ltd., Tokyo (JP)

(72) Inventors: Hayato Akiyama, Tokyo (JP); Masatoshi Takagi, Tokyo (JP); Manabu Harada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 108 days.

(21) Appl. No.: 16/346,184

(22) PCT Filed: Nov. 15, 2017

(86) PCT No.: PCT/JP2017/041124
§ 371 (c)(1),
(2) Date: Apr. 30, 2019

(87) PCT Pub. No.: WO2018/092812
PCT Pub. Date: May 24, 2018

(65) Prior Publication Data
US 2019/0298874 A1    Oct. 3, 2019

(30) Foreign Application Priority Data

Nov. 16, 2016 (JP) .............................. JP2016-223105
Dec. 1, 2016 (JP) .............................. JP2016-233951
Nov. 14, 2017 (JP) .............................. JP2017-218849

(51) Int. Cl.
*A61L 2/20* (2006.01)
*A23L 3/3409* (2006.01)
*B65B 55/10* (2006.01)

(52) U.S. Cl.
CPC ............. *A61L 2/208* (2013.01); *A23L 3/3409* (2013.01); *A61L 2/20* (2013.01); *B65B 55/10* (2013.01);

(Continued)

(58) Field of Classification Search
CPC ........ A61L 2/208; A23L 3/3409; B65B 55/10
See application file for complete search history.

(56) References Cited

U.S. PATENT DOCUMENTS 4,797,255 A    1/1989  Hatanaka et al.
6,085,026 A *  7/2000  Hammons ................. A61L 9/03
                                                  392/390

(Continued)

FOREIGN PATENT DOCUMENTS

JP    S60-220067 A1    11/1985
JP    S63-011163 A1     1/1988

(Continued)

OTHER PUBLICATIONS

*Encyclopedic Dictionary of Chemistry 3*, "Use of Chrome," p. 198, left column (non-official translation) (with English Abstract of Chrome).

(Continued)

*Primary Examiner* — Kevin Joyner
(74) *Attorney, Agent, or Firm* — Burr & Brown, PLLC

(57) ABSTRACT

To provide an apparatus that can gasify a sterilizer containing hydrogen peroxide to produce a gas having a high hydrogen peroxide concentration. The apparatus can stably produce a gas of the sterilizer containing hydrogen peroxide for a long time. A heating surface of a heating body that gasifies the sterilizer is made of chromium. Alternatively, the heating surface of the heating body that gasifies the sterilizer may be made of polytetrafluoroethylene or perfluoroalkoxy fluorocarbon resin, or a chromium plating impregnated with chromium polytetrafluoroethylene or perfluoroalkoxy fluorocarbon resin.

10 Claims, 6 Drawing Sheets

(52) U.S. Cl.
CPC ....... *A61L 2202/15* (2013.01); *A61L 2202/23* (2013.01)

(56) References Cited

U.S. PATENT DOCUMENTS

| | | |
|---|---|---|
| 2002/0159915 A1 | 10/2002 | Zelina et al. |
| 2005/0175500 A1* | 8/2005 | Adams ................. A61L 2/24 422/29 |
| 2008/0226497 A1 | 9/2008 | Dotsch et al. |
| 2009/0074611 A1 | 3/2009 | Monzyk et al. |

FOREIGN PATENT DOCUMENTS

| | | |
|---|---|---|
| JP | H03-224469 A1 | 10/1991 |
| JP | H07-107949 A1 | 4/1995 |
| JP | 3037963 U | 6/1997 |
| JP | H10-127735 A | 5/1998 |
| JP | H10-218134 A1 | 8/1998 |
| JP | H10-258811 A1 | 9/1998 |
| JP | H11-113984 A1 | 4/1999 |
| JP | 2006-036343 A1 | 2/2006 |
| JP | 2006-240969 A1 | 9/2006 |
| JP | 2009-507887 A1 | 2/2009 |
| JP | 2009-508676 A1 | 3/2009 |
| JP | 2010-209458 A1 | 9/2010 |
| JP | 2013-188402 A1 | 9/2013 |
| JP | 2015-050962 A1 | 3/2015 |
| WO | WO 2016/114273 A1 | 7/2016 |

OTHER PUBLICATIONS

International Search Report and Written Opinion (Application No. PCT/JP2017/041124) dated Feb. 13, 2018.

* cited by examiner

GASIFIER FOR STERILIZER

TECHNICAL FIELD

The present invention relates to a gasifier for a sterilizer that produces a gas of a sterilizer used for sterilization of a packaging in an aseptic filling and packaging machine.

BACKGROUND ART

Foods and drinks in various containers produced by aseptic filling and packaging machines are commercially available, such as creamers, brick carton beverages, pouch soups, cup drinks, and PET-bottled beverages. The aseptic filling and packaging machine is a machine that fills a container sterilized in an aseptic atmosphere with a sterilized content and seals the container. Products produced by the aseptic filling and packaging machine can be distributed and stored at room temperature and therefore consume less energy than refrigerated or frozen products, and also taste good. For these reasons, the products produced by the aseptic filling and packaging machine are increasing.

The aseptic filling and packaging machine handles various types of packagings used as containers as described above, and sterilizes different types of packagings in different sterilization processes. In some processes, packagings are irradiated with ultraviolet rays or electron beam. However, sterilizers are generally used to sterilize the surface of the packagings. When packagings such as tubs for creamers or brick cartons are sterilized using a sterilizer, the packagings may be immersed in the sterilizer, or the sterilizer may be sprayed to the packagings. Packagings that are flat and can be dried at relatively high temperatures after immersion are sterilized by immersion. On the other hand, molded containers such as cups or bottles or other packagings such as films that are stretched at high drying temperatures are sterilized by spraying of the sterilizer.

If drops of the sprayed sterilizer are large, the sterilizer can flow down the side of the cup or bottle. The smaller the drops of the sprayed sterilizer, the more uniformly the sterilizer is applied to the surface of the packaging, and the higher the sterilization effect is. In this respect, there has been proposed a method of making drops of the sterilizer finer (Patent Literature 1).

The smaller the drops of the sterilizer on the surface of the packaging, and the more densely the surface of the packaging is covered with the drops of the sterilizer, the higher the sterilization effect is. In this respect, instead of a method of spraying the drops of the sterilizer, there has been proposed a method of gasifying the sterilizer, blasting the gas of the sterilizer to the surface of the packaging, and letting the sterilizer condense on the surface of the packaging (Patent Literature 2). The gasification of the sterilizer is achieved by dripping the sterilizer onto a heating element heated.

Furthermore, there has been proposed a method of efficiently gasifying a large amount of sterilizer by spraying the sterilizer into a heated pipe (Patent Literature 3). Furthermore, there has been proposed a method in which a heat reservoir is provided in the heated pipe (Patent Literature 4).

A hydrogen peroxide solution is used as the sterilizer, any trace amount of heavy metal in the hydrogen peroxide solution causes decomposition of hydrogen peroxide. To prevent this, sodium pyrophosphate or orthophosphoric acid, which have been proven to be safe and effective, are added as a stabilizer to the hydrogen peroxide solution used for sterilization in the aseptic filling and packaging machine (Patent Literature 5). When the hydrogen peroxide solution is gasified, such a stabilizer can be deposited and accumulated on the surface of the heating body that causes the gasification, thereby reducing the efficiency of the gasification of the hydrogen peroxide solution or blocking the nozzle that blasts the gas of the hydrogen peroxide solution to the object to be sterilized. To solve the problems with the deposition of the stabilizer, there has been proposed a method of temporarily gasifying the hydrogen peroxide solution, cooling and passing the resulting gas through a filter, and then gasifying the recovered hydrogen peroxide solution again (Patent Literature 6).

CITATION LIST

Patent Literature

Patent Literature 1: Japanese Patent Laid-open Publication No. 60-220067
Patent Literature 2: Japanese Patent Laid-open Publication No. 63-11163
Patent Literature 3: Japanese Patent Laid-open Publication No. 3-224469
Patent Literature 4: Japanese Patent Laid-open Publication No. 10-218134
Patent Literature 5: Japanese Patent Laid-open Publication No. 2006-240969
Patent Literature 6: Japanese Patent Laid-open Publication No. 10-258811

SUMMARY OF INVENTION

Technical Problem

To sterilize a packaging in an aseptic filling and packaging machine, a gas of a hydrogen peroxide solution is often used. As described in Patent Literatures 2, 3 and 4, the sterilizer is gasified by making the sterilizer come into contact with a heating element. The heating element is made of metal, for example. In particular, stainless steel is used.

The more the gas of the sterilizer blown to the surface of the packaging, and the higher the concentration of the sterilizing constituent in the gas of the sterilizer, the higher the sterilization effect for the packaging is. The amount of the gas of the sterilizer can be increased by raising the temperature of the heating element with which the sterilizer comes into contact when the sterilizer is gasified. However, if the temperature is too high, the sterilizing constituent is decomposed, and the content of the sterilizing constituent in the gasified sterilizer decreases. It is desirable that, even if the temperature of the heating element is raised to improve the efficiency of gasification, the sterilizing constituent in the sterilizer gas is prevented from being decomposed so that the concentration of the sterilizing constituent in the sterilizer gas is kept high.

In addition, if gasification of the hydrogen peroxide solution lasts for a long time, the stabilizer added to the hydrogen peroxide solution can be deposited and accumulated on the heating element as the hydrogen peroxide solution is gasified. The accumulated stabilizer inhibits heat radiation from the surface of the heating element, thereby reducing the efficiency of gasification of the hydrogen peroxide solution. To avoid this, the gasifier for a sterilizer needs to be regularly disassembled and cleaned, which reduces productivity.

To solve the problem with the deposition of the stabilizer, the method disclosed in Patent Literature 6 has been proposed. However, this method involves performing gasification of the hydrogen peroxide solution twice, and the stabilizer is not contained in the hydrogen peroxide solution in the second gasification. Therefore, in the second gasification, the hydrogen peroxide in the solution is decomposed, the concentration of hydrogen peroxide in the produced gas decreases, and therefore the sterilization effect decreases. In addition, since gasification is conducted twice, the energy consumption is high.

The present invention has been devised to solve the problems described above, and an object of the present invention is to provide a gasifier for a sterilizer for a packaging that efficiently produces a gas of a sterilizer containing a high concentration of a sterilizing constituent by reducing decomposition of the sterilizing constituent.

The present invention has been devised to solve the problems described above, and another object of the present invention is to provide a gasifier for a sterilizer that can stable produce a gas of a sterilizer containing a high concentration of hydrogen peroxide as a sterilizing constituent for a long time.

Solution to Problem

A gasifier for a sterilizer according to the present invention is a gasifier that makes a sterilizer containing at least hydrogen peroxide come into contact with a heating surface to gasify the sterilizer, and the heating surface is made of chromium.

In the gasifier for a sterilizer according to the present invention, it is preferable that a surface of the chromium has an arithmetic mean roughness (Ra) of 1.0 μm or less and a ten-point mean roughness of 2.0 μm or less.

A gasifier for a sterilizer according to the present invention is a gasifier that makes a sterilizer containing at least hydrogen peroxide and a stabilizer come into contact with a heating surface to gasify the sterilizer, and the heating surface is made of polytetrafluoroethylene or perfluoroalkoxy fluorocarbon resin, or a chromium plating impregnated with polytetrafluoroethylene or perfluoroalkoxy fluorocarbon resin.

It is preferable that the gasifier for a sterilizer according to the present invention includes a sterilizer supplying portion that sprays the sterilizer to the heating surface and a sterilizer evaporating portion that includes the heating surface, and the heating surface has a cylindrical shape.

In the gasifier for a sterilizer according to the present invention, it is preferable that the sterilizer supplying portion includes a twin-fluid sprayer.

It is preferable that the gasifier for a sterilizer according to the present invention includes a heated air supplying device that introduces heated air provided at an end portion of the sterilizer evaporating portion.

It is preferable that the gasifier for a sterilizer according to the present invention includes a filter provided at an end portion of the sterilizer evaporating portion.

Advantageous Effects of Invention

According to the present invention, a gas of a sterilizer containing a high concentration of hydrogen peroxide used for sterilizing a packaging such as a bottle or cup made of paper or plastics in an aseptic filling and packaging machine that fills the packaging with a beverage or a dairy product can be efficiently produced. The sterilization power of the aseptic filling and packaging machine can be improved by incorporating the gasifier for a sterilizer according to the present invention in the aseptic filling and packaging machine.

Furthermore, according to the present invention, a gas of a sterilizer containing at least hydrogen peroxide used for sterilizing a packaging can be efficiently and stably produced for a long time. As a result, the sterilization power of the aseptic filling and packaging machine for the packaging can be maintained for a long time.

DESCRIPTION OF EMBODIMENTS

In the following, embodiments of the present invention will be described with reference to the drawings.

First Embodiment

Figure 1:
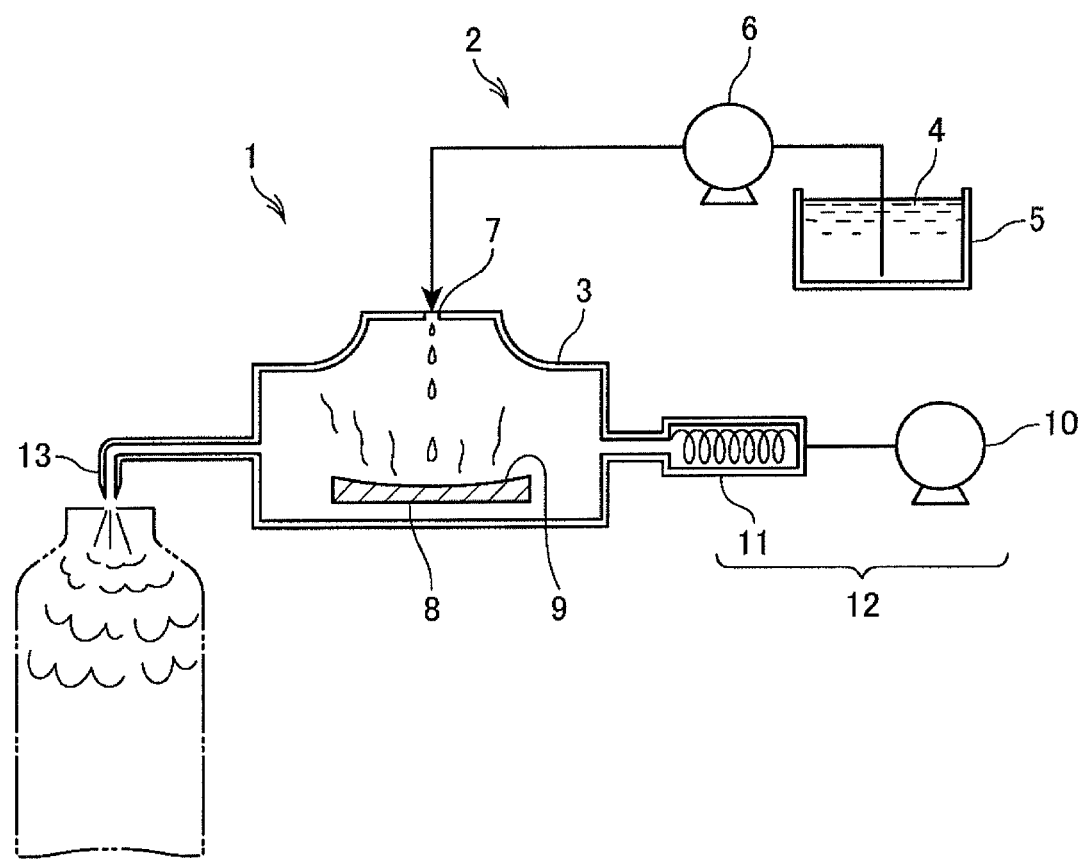
FIG. 1 is a side view of a gasifier for a sterilizer according to a first embodiment of the present invention.

FIG. 1 shows a gasifier 1 for a sterilizer according to a first embodiment of the present invention. The gasifier 1 for a sterilizer includes a sterilizer supplying portion 2, a sterilizer evaporating portion 3, and a heated air supplying device 12. The sterilizer supplying portion 2 includes a tank 5 that stores a sterilizer 4, a dropper 7 that drips the sterilizer 4 into the sterilizer evaporating portion 3, and a pump 6 that feeds the sterilizer 4 to the dropper 7. Furthermore, the sterilizer evaporating portion 3 includes a heating body 8 that gasifies the sterilizer 4 dripped into the sterilizer evaporating portion 3. The heated air supplying device 12 includes a blower 10 that feeds air, and a heating device 11 that heats the air fed by the blower 10.

The dripped sterilizer 4 comes into contact with and is gasified on a heating surface 9 of the heating body 8, and the heating surface 9 is made of chromium. Although the whole of the heating body 8 may be made of chromium, the heating body 8 may be made of iron, stainless steel, a copper alloy, aluminum, an aluminum alloy, zinc or tungsten, and the surface of the heating body 8 may be plated with chromium. The surface of the chromium reacts with oxygen to form chromium oxide, which is passive. Therefore, the surface is extremely stable and does not corrode for a long time even though hydrogen peroxide in the sterilizer 4 at high temperature comes into contact with the surface.

If the surface of the heating body 8 is plated with chromium, the thickness of the plating is appropriately 0.1 µm to 100 µm. Before the plating, the surface of the heating body to be plated with chromium may be plated with copper or nickel. The surface of the chromium plating may be polished to improve the smoothness.

Probably because the heating surface 9 of the heating body 8 is made of chromium, decomposition of hydrogen peroxide is reduced when the hydrogen peroxide in the sterilizer 4 is gasified. Therefore, the amount of hydrogen peroxide in the gas of the sterilizer 4 produced by the gasifier 1 for a sterilizer according to the present invention is increased compared with the heating surface 9 made of stainless steel or the like according to prior art.

The heating surface 9 preferably has an arithmetic mean roughness (Ra) of 1.0 µm or less and a ten-point mean roughness (Rz) of 2.0 µm or less. If Ra is greater than 1.0 µm, or Rz is greater than 2.0 µm, the concentration of hydrogen peroxide in the sterilizer gas decreases. This is probably because, if the surface area of the heating surface 9 is large, the sterilizer is unnecessarily heated when the sterilizer comes into contact with the surface and is gasified, and therefore more hydrogen peroxide in the sterilizer is decomposed.

The heating surface 9 of the heating body 8 that gasifies the dripped sterilizer 4 is made of polytetrafluoroethylene or perfluoroalkoxy fluorocarbon resin or a chromium plating impregnated with polytetrafluoroethylene or perfluoroalkoxy fluorocarbon resin. As the material of the heating body 8, a metal such as iron, stainless steel, a copper alloy, aluminum, an aluminum alloy, zinc or tungsten is used. The heating surface 9 may also be formed by coating the surface of the heating body 8 with polytetrafluoroethylene or perfluoroalkoxy fluorocarbon resin or forming a chromium plating impregnated with polytetrafluoroethylene or perfluoroalkoxy fluorocarbon resin on the surface of the heating body 8.

Polytetrafluoroethylene and perfluoroalkoxy fluorocarbon resin have an anti-stick quality. If the heating surface 9 is made of polytetrafluoroethylene or perfluoroalkoxy fluorocarbon resin or a chromium plating impregnated with polytetrafluoroethylene or perfluoroalkoxy fluorocarbon resin, the anti-stick quality of the heating surface 9 can prevent a stabilizer deposited when the sterilizer 4 comes into contact with the heating surface 9 and is gasified from adhering to the heating surface 9. As a result, the deposited stabilizer can be prevented from being accumulated on the heating surface 9. As a result, even if the gasifier 1 for a sterilizer operates for a long time, the concentration of hydrogen peroxide in the gas of the sterilizer 4 does not decrease.

Polytetrafluoroethylene is a polymer of the monomer tetrafluoroethylene and has a melting point of about 325° C. The perfluoroalkoxy fluorocarbon resin is a copolymer of tetrafluoroethylene and perfluoroether and has a melting point of about 310° C. The surface of the heating body 8 is subjected to a surface treatment such as degreasing, blasting or high-pressure blasting with ceramic particles in order to enhance adhesion, and then is coated with any of these materials by electrostatic powder coating or the like. The heating body 8 coated with polytetrafluoroethylene or perfluoroalkoxy fluorocarbon resin is then baked at about 400° C. to finish the heating surface 9. The coating and baking may be conducted twice or more times. The thickness of the polytetrafluoroethylene or perfluoroalkoxy fluorocarbon resin is desirably 100 µm to 1000 µm. If the thickness is less than 100 µm, pin holes can occur. If the thickness is greater than 1000 µm, heat conduction from the heating body 8 is compromised.

To form the chromium plating impregnated with polytetrafluoroethylene or perfluoroalkoxy fluorocarbon resin on the heating body 8, particles of polytetrafluoroethylene or perfluoroalkoxy fluorocarbon resin are dispersed in the plating solution. The diameter of the particles of polytetrafluoroethylene or perfluoroalkoxy fluorocarbon resin is typically about 1 µm to 5 µm, because the particles can be exposed on and drop off the surface if the diameter is greater than the thickness of the plating. The amount of the particles to be dispersed in the plating solution is about 15% to 60%, preferably 25% to 40% by volume fraction in the plating. If the volume fraction is lower than 15%, the anti-stick quality is poor. If the volume fraction is higher than 60%, the adhesion between the plating coating and the heating body 8 is poor.

When the chromium plating impregnated with polytetrafluoroethylene or perfluoroalkoxy fluorocarbon resin is formed on the surface of the heating body 8, the thickness of the plating is appropriately 1 µm to 100 µm. Before the plating, the surface of the heating body 8 to be plated may be plated with copper or nickel, for example. The surface of the chromium plating may be polished to improve the smoothness.

The sterilizer 4 contains at least hydrogen peroxide. The content of the hydrogen peroxide is appropriately 0.5% by mass to 65% by mass. If the content is lower than 0.5% by mass, the sterilizing power can be insufficient. If the content is higher than 65% by mass, it is difficult to safely handle the sterilizer 4. A more preferable range is 0.5% by mass to 40% by mass. If the content is equal to or lower than 40% by mass, the sterilizer 4 can be more easily handled, and the amount of the hydrogen peroxide remaining on the packaging sterilized can be reduced because of the low concentration of hydrogen peroxide in the sterilizer 4.

The sterilizer 4 also contains a stabilizer to prevent decomposition of hydrogen peroxide. Preferably, the stabilizer contained in the sterilizer 4 is sodium pyrophosphate or orthophosphoric acid, which are food additives for sterilizing packagings for food products specified by the Minister of Health, Labour and Welfare. However, an inorganic compound containing phosphorous such as sodium hydrogen pyrophosphate or a phosphonate chelating agent such as aminotrimethylphosphonic acid, alkylidenediphosphonate may also be used, for example. The content of the stabilizer is typically equal to or lower than 40 ppm.

Although the sterilizer 4 contains water, the sterilizer 4 may contain one or more of alcohols such as methyl alcohol, ethyl alcohol, isopropyl alcohol, n-propyl alcohol and butyl alcohol, ketones such as acetone, methyl ethyl ketone and acetylacetone, and glycor ethers, for example.

The sterilizer 4 may further contain an additive agent such as a compound having a sterilizing effect such as peracetic acid, acetic acid, a chlorine compound or ozone, a cationic surface active agent and a non-ionic surface active agent.

The sterilizer 4 stored in the tank 5 is supplied to the dropper 7 by the action of the pump 6. The amount of the supplied sterilizer 4 is arbitrary and is determined based on the required amount of the gas of the sterilizer. If one gasifier 1 is not enough to supply the required amount of the gas of the sterilizer, a plurality of gasifiers 1 is used. The amount of the sterilizer dripped by the dropper 7 is also determined based on the required amount of the gas of the sterilizer. The amount of the gas produced on the heating surface 9 is determined by the temperature and heat capacity of the heating body 8.

The temperature of the heating surface 9 of the heating body 8 that gasifies the sterilizer 4 is set at 130° C. to 260° C. If the temperature is lower than 130° C., gasification is hardly achieved. If the temperature is higher than 260° C., polytetrafluoroethylene or perfluoroalkoxy fluorocarbon resin can be decomposed. The heating surface 9 of the heating body 8 may be a planar surface and horizontal or inclined, or may be a curved surface such as a concave or convex surface. The heating surface 9 of the heating body 8 can have any shape as far as the sterilizer 4 can come into contact with the heating surface 9 of the heating body 8 and be gasified. The heating body 8 can have any size and thickness. The greater the volume of the heating body 8, the higher the heat capacity of the heating body 8. The higher heat capacity of the heating body 8 is advantageous for gasification of the sterilizer 4 but leads to a larger size of the gasifier 1 for a sterilizer.

As far as the heating body 8 can be heated to a desired temperature, the heating body 8 can be heated in any way, such as energizing the heating body 8 to make the heating body 8 itself generate heat, embedding a heater in the heating body 8, placing the heating body 8 in contact with a heater, or heating the heating body 8 with an induction heating device.

The gas of the sterilizer 4 produced in the sterilizer evaporating portion 3 is discharged through an air blasting port 13 by the action of heated air fed from the heated air supplying device 12 and is used to sterilize a packaging such as a bottle. Any amount of heated air can be supplied. However, as the amount of the supplied heated air increases, the concentration of hydrogen peroxide in the gas of the sterilizer 4 decreases, and as a result, the sterilizing power of the sterilizer gas can be poor. The temperature of the heated air is set at 130° C. to 260° C. If the temperature is lower than 130° C., the gasified sterilizer 4 can be liquefied before being used for sterilization, so that the surface area of the object to be sterilized can decrease, and the sterilization effect can deteriorate. It is desirable that the gas of the sterilizer 4 comes into contact with the object to be sterilized and forms fine mist on the object, and the temperature of the heated air is set at an appropriate temperature for achieving this. As the temperature of the heated air becomes higher, some objects to be sterilized can be deformed. Thus, the temperature of the heated air varies with the object to be sterilized. If the temperature is higher than 260° C., polytetrafluoroethylene or perfluoroalkoxy fluorocarbon resin can be decomposed. The gas of the sterilizer 4 is discharged through the air blasting port 13 by the action of the heated air. The discharged gas of the sterilizer is blown to the packaging such as a bottle to sterilize the packaging.

Second Embodiment

Figure 2:
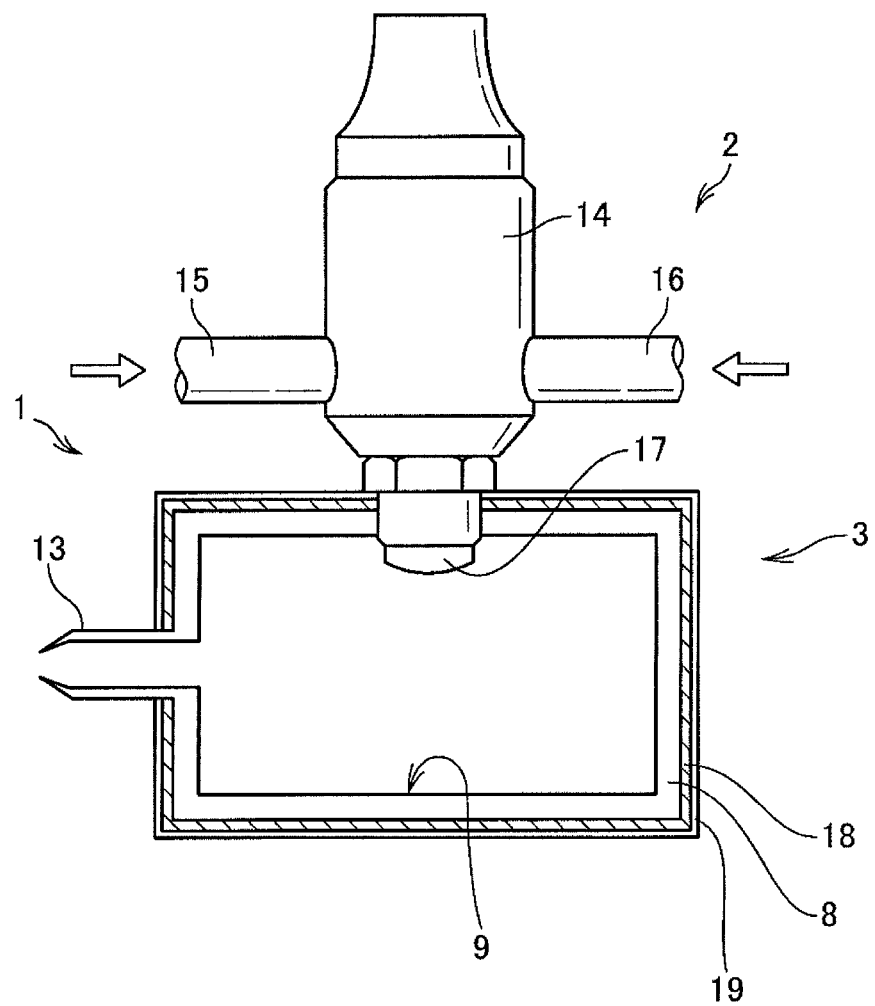
FIG. 2 is a side view of a gasifier for a sterilizer according to a second embodiment of the present invention.

FIG. 2 shows a gasifier 1 for a sterilizer according to a second embodiment of the present invention. The gasifier 1 for a sterilizer includes a sterilizer supplying portion 2 and a sterilizer evaporating portion 3. The sterilizer supplying portion 2 includes a spraying device 14, and the spraying device 14 supplies the sterilizer 4 to the sterilizer evaporating portion 3. An inner surface of the sterilizer evaporating portion 3 is formed as a heating body 8.

The spraying device 14 receives a sterilizer 4 through a sterilizer supply port 15 and compressed air through a compressed air supply port 16. The spraying device 14 is a twin-fluid sprayer, and sprays the sterilizer 4 in the form of a mist to the inner surface of the sterilizer evaporating portion 3 through a spray nozzle 17. The sprayed sterilizer 4 comes into contact with a heating surface 9 of the heating body 8 and is gasified. The produced gas of the sterilizer 4 is discharged through an air blasting port 13 under the pressure of the compressed air.

The diameter of the air blasting port 13 for the gas of the sterilizer 4 can be arbitrarily set and can be set at 2 mm to 200 mm. The smaller the diameter, the higher the blasting pressure of the produced gas of the sterilizer 4. By adjusting the blasting pressure, the intensity of blasting of the gas of the sterilizer, the mist of the condensate of the sterilizer gas, or a mixture thereof onto the surface of the object to be sterilized can be adjusted. For example, if the object to be sterilized is a deep cup, the sterilizer can be blown with high intensity. If the object to be sterilized is a shallow container, the sterilizer can be blown with low intensity. If the air blasting port 13 is long, the gas of the sterilizer 4 may cool and condense. In such a case, the periphery of the air blasting port 13 may be heated.

The sterilizer 4, the materials of the heating body 8 and the heating surface 9 and the like are the same as those in the first embodiment. The second embodiment differs from the first embodiment in that the sterilizer is supplied to the sterilizer evaporating portion 3 by spraying a mist of the sterilizer, the heating body 8 forms the inner surface of the sterilizer evaporating portion 3, and the gasifier 1 does not include the heated air supplying device 12.

The inner surface of the sterilizer evaporating portion 3 is formed as the heating body 8 as described above. The sterilizer evaporating portion 3 is provided, on an outer surface thereof, with a heater 18 for heating the heating body 8, and the heater 18 is provided, on an outer surface thereof, with an outer covering 19 for providing heat insulating properties and protection for the heater 18. Although FIG. 2 shows that the heater 18 heats the heating body 8, the heating body 8 can be heated in any way as in the first embodiment.

With regard to operating conditions of the spraying device 14, the pressure of the compressed air is adjusted to fall within a range of 0.05 MPa to 0.6 MPa, for example. The sterilizer 4 may be supplied by gravity or under pressure using the pump 6. The amount of the supplied sterilizer 4 can be arbitrarily set, and the sterilizer may be supplied at a rate of 1 g/min to 100 g/min, for example.

Third Embodiment

Figure 3:
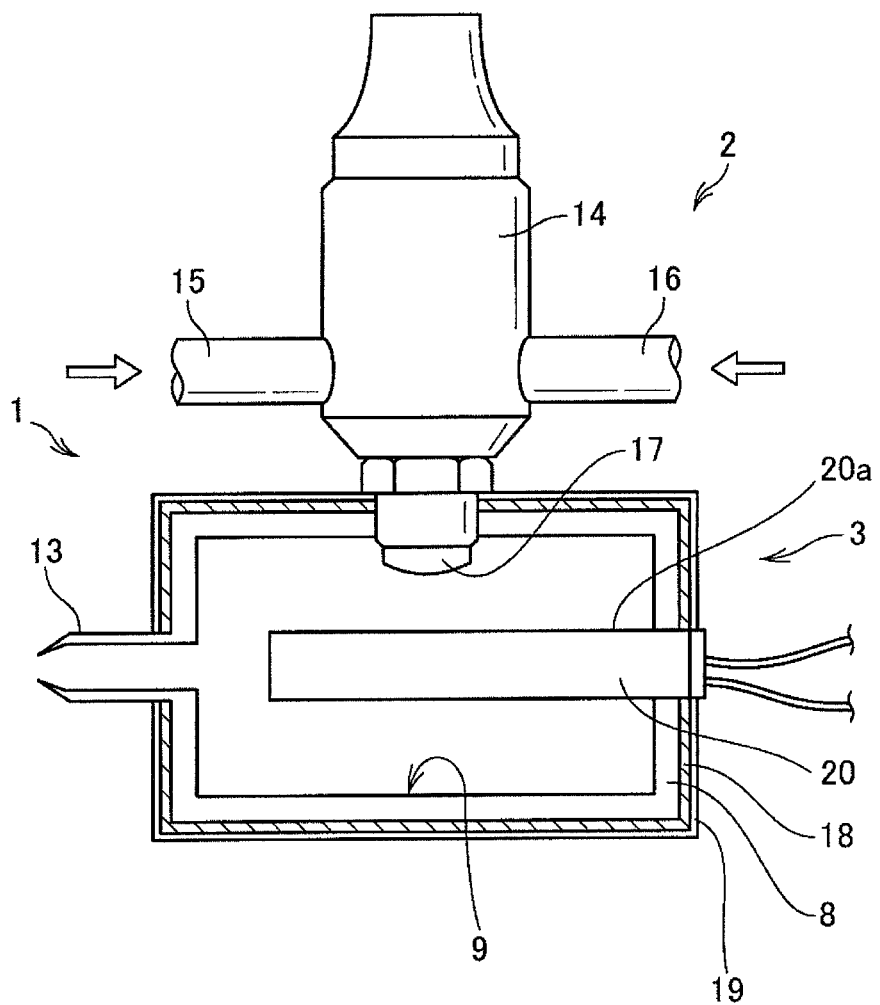
FIG. 3 is a side view of a gasifier for a sterilizer according to a third embodiment of the present invention.

FIG. 3 shows a gasifier 1 for a sterilizer according to a third embodiment of the present invention. The third embodiment differs from the second embodiment in that a bar-shaped heating body 20 is provided in a sterilizer evaporating portion 3 in addition to the heating body 8 provided on the inner surface of the sterilizer evaporating portion 3. By providing the bar-shaped heating body 20, the gasification power of the gasifier 1 for a sterilizer can be enhanced to increase the amount of the sterilizer gasified.

A heating surface 20*a* of the bar-shaped heating body 20 is made of chromium. The bar-shaped heating body 20 itself may be made of chromium, or the bar-shaped heating body 20 made of another material may be plated with chromium. In this respect, the bar-shaped heating body 20 is the same as the heating body 8 in the first embodiment. The bar-shaped heating body 20 may be heated by a heater embedded in the bar-shaped heating body 20 or a heating medium circulating in the bar-shaped heating body 20. The bar-shaped heating body 20 is heated to 130° C. to 450° C. The bar-shaped heating body 20 can have any shape such as a bar, a plate or a coil.

The heating surface 20a of the bar-shaped heating body 20 is made of polytetrfluoroethylene or perfluoroalkoxy fluorocarbon resin or a chromium plating impregnated with polytetrafluoroethylene or perfluoroalkoxy fluorocarbon resin. In this respect, the bar-shaped heating body 20 is the same as the heating body 8 in the first embodiment. The bar-shaped heating body 20 may be heated by a heater embedded in the bar-shaped heating body 20 or a heating medium circulating in the bar-shaped heating body 20. As with the heating body 8, the bar-shaped heating body 20 is heated to 130° C. to 260° C. The bar-shaped heating body 20 can have any shape such as a bar, a plate or a coil.

Fourth Embodiment

Figure 4:
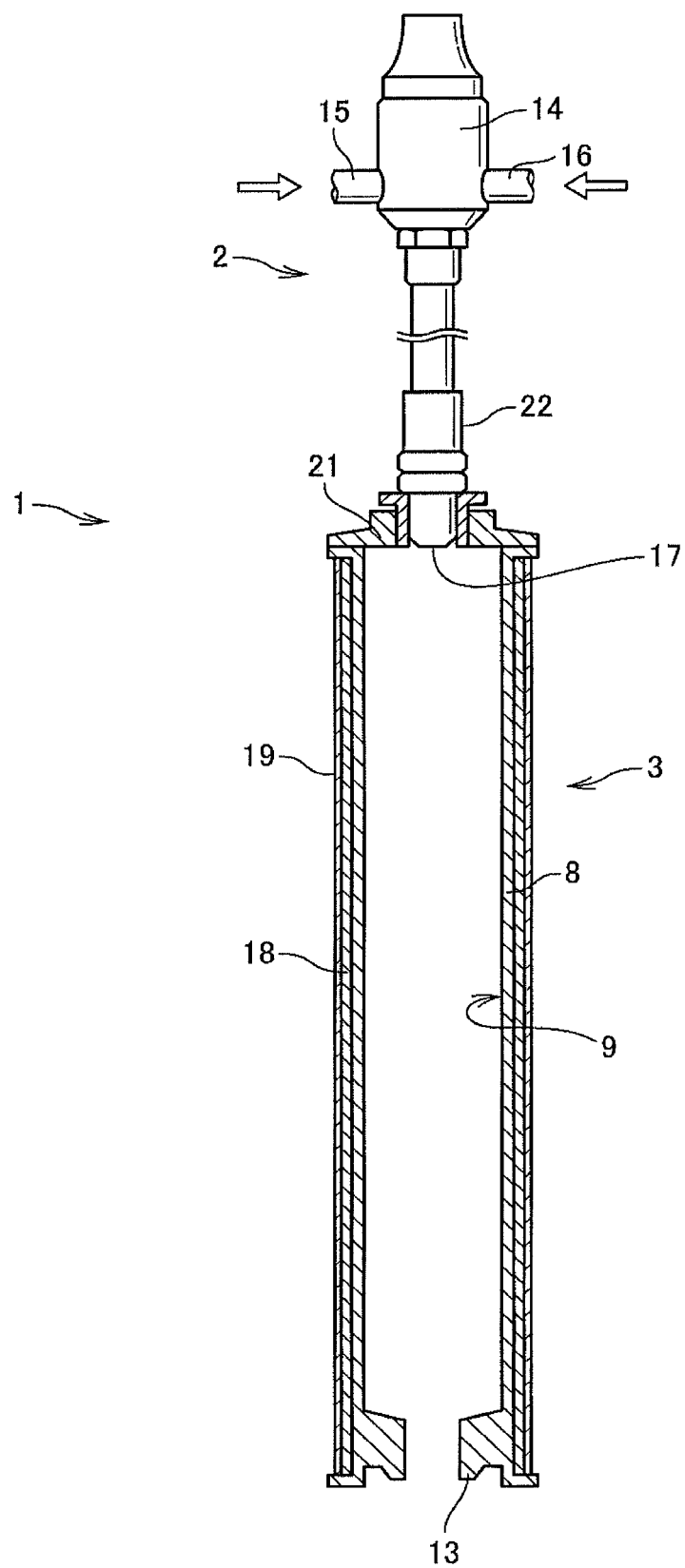
FIG. 4 is a side view of a gasifier for a sterilizer according to a fourth embodiment of the present invention.

FIG. 4 shows a gasifier 1 for a sterilizer according to a fourth embodiment of the present invention. The fourth embodiment provides more efficient gasification of a sterilizer 4 than the first to third embodiments. A spraying device 14 provided on a sterilizer supplying portion 2 is a twin-fluid sprayer that is similar to those in the second and third embodiments. The sterilizer 4 is supplied from a tank (not shown) for the sterilizer 4 to the spraying device 14 through a sterilizer supply port 15, and compressed air is supplied to the spraying device 14 through a compressed air supply port 16. The sterilizer 4 passes through an extension pipe 22 and then is sprayed into a sterilizer evaporating portion 3 through a spray nozzle 17. The sterilizer 4 is the same as that in the first embodiment. The operating conditions of the spraying device 14 are the same as those in the second embodiment. The extension pipe 22 is provided to prevent heat in the sterilizer evaporating portion 3 from being conducted to the spraying device 14 through a plug 21, which closes the top of the sterilizer evaporating portion 3, to raise the temperature of the main unit of the spraying device 14.

The sterilizer evaporating portion 3 includes a heating body 8 on an inner surface thereof, a heater 18 for heating the heating body 8 on an exterior thereof, and an outer covering 19 for providing heat insulating properties and protection for the heater 18 on an exterior of the heater 18. Although FIG. 4 shows that the heater 18 heats the heating body 8, the heating body 8 can be heated in any way as in the first embodiment. The heating body 8 is heated to 130° C. to 260° C., and the sterilizer 4 sprayed through a spray nozzle 17 comes into contact with the heating surface 9 and is gasified. Operating conditions of the spraying device 14 are the same as those in the second embodiment.

The heating surface 9 of the heating body 8 is made of chromium. The heating body 8 itself may be made of chromium, or the heating body 8 may be made of iron, stainless steel, a copper alloy, aluminum, an aluminum alloy, zinc, tungsten or the like and plated with chromium. The plating is conducted in the same manner as in the first embodiment. The heating surface 9 made of chromium is formed by plating the heating body 8 with chromium.

The heating surface 9 of the heating body 8 is made of polytetrafluoroethylene or perfluoroalkoxy fluorocarbon resin or a chromium plating impregnated with polytetrafluoroethylene or perfluoroalkoxy fluorocarbon resin. The heating surface 9 is formed in the same manner as in the first embodiment.

The sterilizer 4 is sprayed in a circular pattern through the spray nozzle 17, and therefore the heating body 8 preferably has a circular cylindrical shape. However, the heating body 8 may have a polygonal cylindrical shape. The diameter of the cylinder needs to be enough large to avoid the internal pressure of the sterilizer evaporating portion 3 from being excessively raised by the compressed air used to spray the sterilizer 4. On the other hand, the cylinder has to have a diameter that ensures that the sprayed mist of the sterilizer 4 comes into contact with the heating surface 9. The length of the cylinder is also determined so as to meet these conditions.

The sterilizer 4 having come into contact with the heating surface 9 of the heating body 8 and been gasified is discharged through an air blasting port 13 under the pressure of the compressed air. The air blasting port 13 may be oriented to face the object to be sterilized so that the discharged gas of the sterilizer 4 can be directly blasted to the packaging, which is the object to be sterilized. However, as shown in FIG. 5, a heated air supplying device 12 for introducing heated air may be provided at an end portion of the sterilizer evaporating portion 3, and the gas of the sterilizer 4 discharged from the air blasting port 13 and the heated air supplied from the heated air supplying device 12 may be mixed in a conduit 23 and then blown to the packaging.

Figure 5:
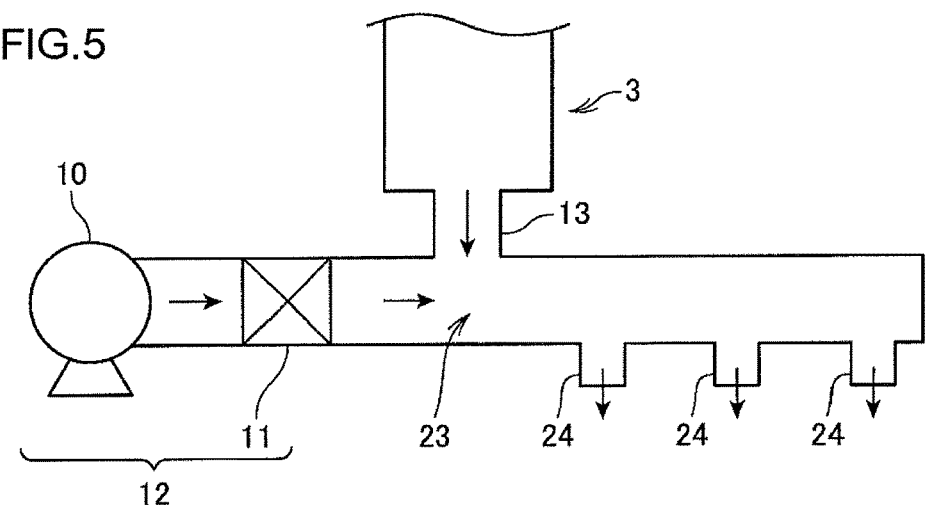
FIG. 5 shows a heated air supplying device incorporated in any gasifier for a sterilizer according to the present invention.

As shown in FIG. 5, the gas of the sterilizer 4 produced in the sterilizer evaporating portion 3 and discharged through the air blasting port 13 may be mixed in the conduit 23 with air blown by a blower 10 and heated by a heating device 11, and then blown to the object to be sterilized through a sterilizer gas blasting port 24. Instead of the single sterilizer evaporating portion 3, a plurality of sterilizer evaporating portions 3 may be coupled to the conduit 23. The number of sterilizer gas blasting ports 24 can be arbitrarily set. The heating device 11 heats the air to 130° C. to 300° C. The temperature of the heated air is restricted by the object to be sterilized, as in the first embodiment. The heated air does not come into contact with the heating surface 9, and therefore, there is no need to consider the decomposition of polytetrafluoroethylene or perfluoroalkoxy fluorocarbon resin.

Figure 6:
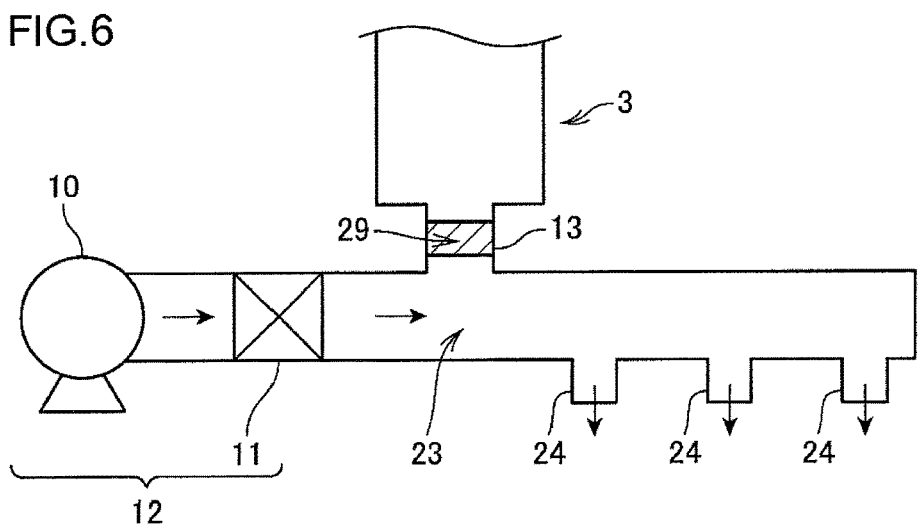
FIG. 6 show a mixing device for mixing a gas of a sterilizer and heated air that is provided with a filter at an air blasting port of any gasifier for a sterilizer according to the present invention.
Figure 7:
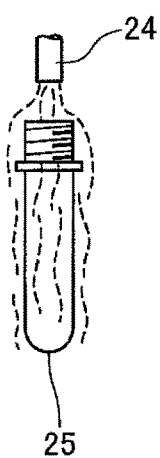
FIG. 7 is a diagram for illustrating a step of blowing, to a preform, a sterilizer gas produced by the gasifier for a sterilizer according to the present invention.

As shown in FIG. 6, the air blasting port 13 at the end of the sterilizer evaporating portion 3 is desirably provided with a filter 29 to capture any deposited stabilizer. This is because the stabilizer can adhere to the interior of the conduit 23 as the gas flows to the sterilizer gas blasting port 24 and block the conduit 23, although the stabilizer used does not pose any hygienic problem. The filter 29 can be any filter that has a heat resistance of 260° C. and can capture the deposited stabilizer, such as a ceramic filter that is made of alumina, zirconium oxide or titanium oxide and has an average pore size of 0.1 μm to 20 μm, or a nonwoven fabric of an inorganic material or cellulose, for example.

The gas of the sterilizer 4 blasted through the sterilizer gas blasting port 24 may be blown to a preform 25, as shown in FIG. 6. The gas or mist of the sterilizer 4 or a mixture thereof comes into contact with or adheres to the inner and outer surfaces of the preform 25 and kills bacteria or the like on the surfaces of the preform 25.

Figure 8:
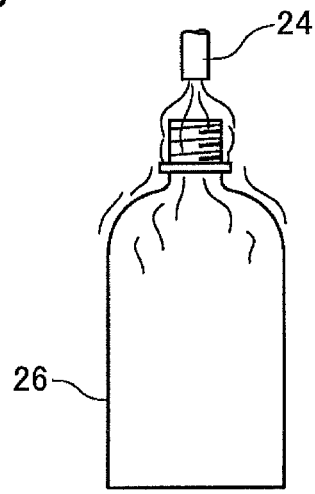
FIG. 8 is a diagram for illustrating a step of blowing, to a bottle, a sterilizer gas produced by the gasifier for a sterilizer according to the present invention.

The gas of the sterilizer 4 blasted through the sterilizer gas blasting port 24 may be blown to a bottle 26, as shown in FIG. 8. The gas or mist of the sterilizer 4 or a mixture thereof comes into contact with or adheres to the inner and outer surfaces of the bottle 26 and kills bacteria or the like on the surfaces of the bottle 26.

Figure 9:
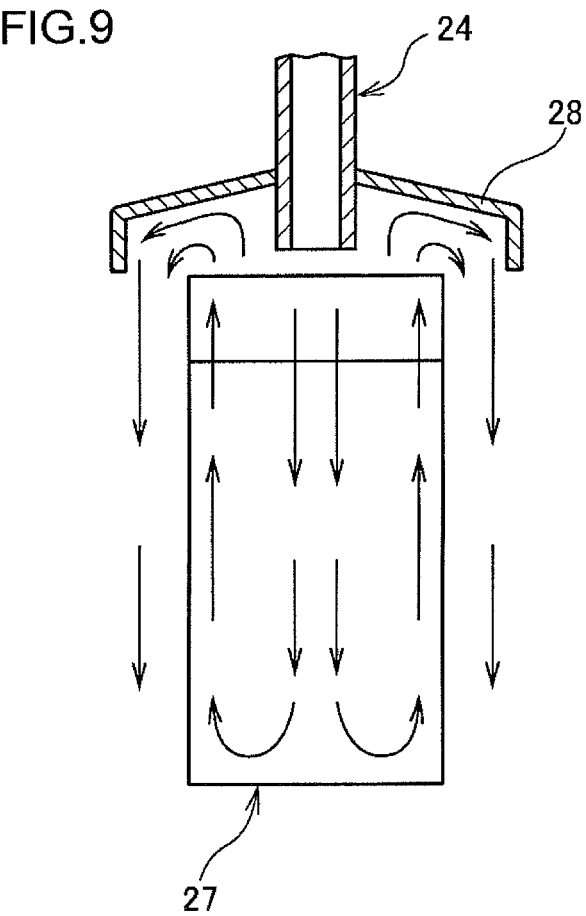
FIG. 9 is a diagram for illustrating a step of blowing, to a paper container, a sterilizer gas produced by the gasifier for a sterilizer according to the present invention.

The gas of the sterilizer 4 blasted through the sterilizer gas blasting port 24 may be blown to a gable-top paper container 27 with a closed bottom, as shown in FIG. 9. The gas or mist of the sterilizer 4 or a mixture thereof comes into contact with or adheres to the inner and outer surfaces of the paper container 27 and kills bacteria or the like on the surfaces of the paper container 27. For a container having a wide opening like the paper container 27, an umbrella-shaped member 28 that surrounds the sterilizer gas blasting port 24 may be provided. Any gas or mist of the sterilizer 4 or mixture thereof that spills out of the paper container collides with the umbrella-shaped member 28 and flows to the edge and outside of the paper container 27, so that the end surface and outer surface of the paper container 27 can be efficiently sterilized. The umbrella-shaped member 28 can also be provided when the preform 25 or the bottle 26 is sterilized. The object to be sterilized can have any other shape, such as a film, a sheet, a tray or a cup.

EXAMPLES

In the following, examples of the present invention will be described.
(Method of Operation)

The gasifier 1 for a sterilizer according to the fourth embodiment was used. As the sterilizer 4, a hydrogen peroxide solution containing 35% by mass of hydrogen peroxide was supplied to the sterilizer supply port 15 of the spraying device 14, which is the twin-fluid sprayer, at a rate of 2.5 g/min. Compressed air at 0.15 MPa was supplied to the compressed air supply port 16. The heating body 8 was made of SUS316, and the surface of the heating body 8 was plated with chromium to form the heating surface 9. The temperature of the heating body 8 was set at 250° C. The thickness of the chromium plating was 3 µm to 5 µm. Ra was 0.413 µm, and Rz was 1.631 µm. The gasifier 1 prepared as described above is an example. Furthermore, a gasifier 1 having a heating surface 9 made of SUS316 was prepared as a comparative example 1, a gasifier 1 having a heating surface 9 made of SUS316L was prepared as a comparative example 2, and a gasifier 1 having a heating surface 9 made of brass was prepared as a comparative example 3. The surface of SUS316 had an Ra of 0.522 µm and an Rz of 2.013 µm, the surface of SUS316L had an Ra of 0.446 µm and an Rz of 1.544 µm, and the surface of brass had an Ra of 1.015 µm and an Rz of 7.593 µm.
(Method of Measurement)

The concentration of hydrogen peroxide at the air blasting port 13 was measured with a portable gas detector available from ATI. At the air blasting port 13, the blasted gas was cooled, and the resulting hydrogen peroxide solution was collected. In this process, although not all the hydrogen peroxide was able to be collected, and some hydrogen peroxide dissipated, the concentration of hydrogen peroxide in the collected hydrogen peroxide solution was measured.
(Measurement of Sterilization Effect)

A preform 25 having a weight of 20 g that is intended for a 500 ml bottle was used. $10^4$, $10^5$ and $10^6$ *B. atrophaeus* ATCC9372 spores were put at three points on the inner surface of a middle portion of the preforms 25, and the preforms 25 were allowed to air-dry. A gas of the hydrogen peroxide solution was blown through the air blasting port 13 to the inner surface of the bacteria-contaminated preform 25. Then, aseptic heated air at 100° C. was blown to the inner surface of the preform 25. Then, the bacteria on the inner surface of the preform 25 was removed by wiping and transferred to an agar medium, cultivation was performed at 37° C. for one week, and the surviving bacteria count was measured. The result was expressed as follows: sterilization effect (LRV)=log(adhering bacteria count)/(surviving bacteria count).

Results of Example and Comparative Examples

Table 1 shows the concentration of hydrogen peroxide in the produced gas, the concentration of hydrogen peroxide in the collected hydrogen peroxide solution, and the sterilization effect for the example 1 and the comparative examples 1 to 3.

TABLE 1

| | Hydrogen Peroxide Concentration of Produced Hydrogen Peroxide Gas (ppm) | Hydrogen Peroxide Concentration of Collected Hydrogen Peroxide Solution (ppm) | Sterilization Effect |
|---|---|---|---|
| Example 1 | 623 | 48.5 | 6.2 |
| Comparative Example 1 | 535 | 40.3 | 5.3 |
| Comparative Example 2 | 569 | 45.4 | 5.7 |
| Comparative Example 3 | 380 | 35.8 | 4.8 |

The result shows that the heating surface 9 of the gasifier 1 for a sterilizer according to the example 1 described above, which was made of chromium, produced a gas having a higher hydrogen peroxide concentration when a hydrogen peroxide solution was gasified and provided a higher sterilization effect than the conventional heating surface 9 made of brass or stainless steel such as SUS316 or SUS316L.

Other examples of the present invention will be described below.
(Method of Operation)

Gasifiers 1 for a sterilizer according to the fourth embodiment shown in FIG. 4 were used. For one gasifier 1, the heating body 8 on the inner surface of the sterilizer evaporating portion 3 was made of SUS316, and the heating body 8 was coated with 100 µm of polytetrafluoroethylene to form the heating surface 9. The gasifier 1 prepared in this way was an example 2. For another gasifier 1, the heating body 8 was made of SUS316 and coated with a chromium plating having a thickness of 50 µm and containing 25% of polytetrafluoroethylene by volume fraction. The gasifier 1 prepared in this way was an example 3. Furthermore, a gasifier 1 having a heating surface 9 made of SUS316 was prepared as a comparative example 4, a gasifier having a heating surface 9 made of SUS316L was prepared as a comparative example 5, and a gasifier 1 having a heating surface 9 made of brass was prepared as a comparative example 6. The heating bodies 8 of these gasifiers 1 were heated to 230° C.

As the sterilizer 4, a hydrogen peroxide solution containing 35% by mass of hydrogen peroxide and a stabilizer was supplied to the sterilizer supply port 15 of the spraying device 14 at a rate of 2.5 g/min. Compressed air at 0.15 MPa was supplied to the compressed air supply port 16. As the spraying device 14, twin-fluid sprayer was used. The gasifiers 1 for a sterilizer were operated for 500 hours under the conditions described above, and then the measurements described below were made.

The method of measurement and the measurement of the sterilization effect were the same as those in the example 1.

Results of Examples and Comparative Examples

Table 2 shows the concentration of hydrogen peroxide in the produced gas, the concentration of hydrogen peroxide in the collected hydrogen peroxide solution, and the sterilization effect for the examples 2 and 3 and the comparative examples 4 to 6. In addition, adhesion of the stabilizer to the heating surface 9 was also checked.

TABLE 2

| | Hydrogen Peroxide Concentration of Produced Hydrogen Peroxide Gas (ppm) | Hydrogen Peroxide Concentration of Collected Hydrogen Peroxide Solution (ppm) | Sterilization Effect | Adhesion of Stabilizer |
|---|---|---|---|---|
| Example 2 | 580 | 45.5 | 6 | Absence |
| Example 3 | 585 | 47.0 | 6.1 | Absence |
| Comparative Example 4 | 460 | 38.3 | 5.3 | Presence |
| Comparative Example 5 | 475 | 39.5 | 5.7 | Presence |
| Comparative Example 6 | 310 | 32.8 | 4.8 | Presence |

The result shows that the heating surfaces 9 of the gasifiers 1 for a sterilizer according to the examples described above, which were made of polytetrafluoroethylene or a chromium plating impregnated with polytetrafluoroethylene, had no stabilizer adhering thereto after operation for a long time, and produced a gas having a higher hydrogen peroxide concentration when a hydrogen peroxide solution was gasified and provided a higher sterilization effect than the conventional heating surface 9 made of brass or stainless steel such as SUS316 or SUS316L.

Although the present invention has been described above, the present invention is not limited to the embodiments described above, and various modifications can be made without departing from the spirit of the present invention.

REFERENCE SIGNS LIST 1 gasifier for sterilizer
2 sterilizer supplying portion
3 sterilizer evaporating portion
8 heating body
9 heating surface
12 heated air supplying device
14 spraying device
29 filter

The invention claimed is:

1. An apparatus for gasifying a sterilizer, the apparatus comprising:
a sterilizer supplying portion that supplies the sterilizer to the apparatus for gasifying;
a sterilizer evaporating portion that is supplied the sterilizer from the sterilizer supplying portion;
a heating surface that gasifies the sterilizer by contacting the sterilizer, the heating surface being an inner surface of the sterilizer evaporating portion; and
a source of hydrogen peroxide as the sterilizer;
wherein the heating surface is made of chromium and has an arithmetic mean roughness (Ra) of 1.0 μm or less and a ten-point mean roughness of 2.0 μm or less.

2. The gasifier for a sterilizer according to claim 1, wherein the sterilizer supplying portion is configured to spray the sterilizer to the heating surface included in the sterilizer evaporating portion, and wherein the heating surface has a cylindrical shape.

3. The gasifier for a sterilizer according to claim 2, wherein the sterilizer supplying portion includes a twin-fluid sprayer.

4. The gasifier for a sterilizer according to claim 2, further comprising a heated air supplying device that introduces heated air provided at an end portion of the sterilizer evaporating portion.

5. The gasifier for a sterilizer according to claim 2, further comprising a filter provided at an end portion of the sterilizer evaporating portion.

6. An apparatus for gasifying a sterilizer, the apparatus comprising:
a sterilizer supplying portion that supplies the sterilizer to the apparatus for gasifying;
a sterilizer evaporating portion that is supplied the sterilizer from the sterilizer supplying portion;
a heating surface that gasifies the sterilizer by contacting the sterilizer, the heating surface being an inner surface of the sterilizer evaporating portion; and
a source of hydrogen peroxide as the sterilizer;
wherein the heating surface is made of a chromium plating impregnated with polytetrafluoroethylene or perfluoroalkoxy fluorocarbon resin.

7. The gasifier for a sterilizer according to claim 6, wherein the sterilizer supplying portion is configured to spray the sterilizer to the heating surface included in the sterilizer evaporating portion, and wherein the heating surface has a cylindrical shape.

8. The gasifier for a sterilizer according to claim 7, wherein the sterilizer supplying portion includes a twin-fluid sprayer.

9. The gasifier for a sterilizer according to claim 7, further comprising a heater air supplying device that introduces heated air provided at an end portion of the sterilizer evaporating portion.

10. The gasifier for a sterilizer according to claim 7, further comprising a filter provided at an end portion of the sterilizer evaporating portion.

* * * * *